US00PP12681P2

(12) United States Plant Patent
Olesen et al.

(10) Patent No.: US PP12,681 P2
(45) Date of Patent: Jun. 11, 2002

(54) ROSE PLANT NAMED 'POULHARMU'

(75) Inventors: L. Pernille Olesen; Mogens N. Olesen, both of Fredensborg (DK)

(73) Assignee: Poulsen Roser Aps, Fredensborg (DK)

( * ) Notice: Subject to any disclaimer, the term of this patent is extended or adjusted under 35 U.S.C. 154(b) by 0 days.

(21) Appl. No.: 09/274,687

(22) Filed: Mar. 24, 1999

(51) Int. Cl.[7] ..... A01H 5/00

(52) U.S. Cl. ..... Plt./108

(58) Field of Search ..... Plt./108, 102

*Primary Examiner*—Bruce R. Campell
*Assistant Examiner*—June Hwu

(57) ABSTRACT

A new garden rose plant which has abundant, orange-red flowers, blooms continuously and has attractive, disease resistant foliage. This new and distinct variety has shown to be uniform and stable in the resulting generations from asexual propagation.

1 Drawing Sheet

SUMMARY OF THE INVENTION

The present invention constitutes a new and distinct variety of garden rose plant which originated from a controlled crossing between an unnamed seedling and an unnamed seedling. The two parents were crossed and the resulting seeds were planted in a controlled environment. The new variety is named 'POULharmu'.

The new rose may be distinguished from its seed parent, an unnamed seedling (non-patented), by the following combination of characteristics:

1. The seed parent is a low, spreading ground cover rose; whereas, 'POULharmu' is taller and has a shrub habit;
2. The blooms of the seed parent are pink; whereas, 'POULharmu' has orange-red blooms.

The new variety may be distinguished from its pollen parent, unnamed seedling, created by the same inventors, by the following combination of characteristics:

1. The pollen parent is a patio rose, and is smaller in habit when compared to 'POULharmu';
2. The leaflets of the pollen parent are much smaller than the leaflets of 'POULharmu';
3. The blooms of the pollen parent are smaller when compared to the blooms of 'POULharmu'.

The objective of the hybridization of this rose variety for nursery and garden use was to create a new and distinct variety with unique qualities, such as:

1. Uniform and abundant flowers;
2. Vigorous, compact growth;
3. Continuous blooming throughout the growing season;
4. Resistance to black-spot and mildew.

This combination of qualities is not present in previously available commercial cultivars of this type and distinguishes 'POULharmu' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULharmu' was selected by the inventors in the Spring 1993 as a single plant from the progeny of the aforementioned hybridization.

Asexual reproduction of 'POULharmu' by cuttings and traditional budding was first done by L. Pernille and Mogens N. Olesen in August 1993. This initial and other subsequent propagations conducted in controlled environments have demonstrated that the characteristics of 'POULharmu' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULharmu'. The variety illustrated in SHEET 1 indicates the variety known as 'POULharm' prior to change in designation to 'POULharmu' as mandated by the European Union Plant Breeder's Right Office. Specifically illustrated in SHEET 1:

1. Stem showing branching and the attachment of leaves, buds, and peduncles;
2. Flower bud, partially opened bud, and open bloom;
3. Flower petals, detached;
4. Sepals, receptacle, and pedicel;
5. Flowering stem as well as a bare stem exhibiting thorns;
6. Leaves.

DETAILED DESCRIPTION OF THE VARIETY

The following is a description of 'POULharmu', as observed in its outdoor growth in a field nursery in Jackson County, Oreg. Observations were conducted during October, 1998, on an eighteen month old plant. Color references are made using The Royal Horticultural Society (London, England) Colour Chart, 1995, except where common terms of color are used.

For a comparison, several physical characteristics of the rose variety 'POULans', a shrub rose variety from the same inventors described and illustrated in U.S. Plant Pat. No. 9,664 and issued on Oct. 22, 1996 are compared to 'POULharmu' in Chart 1.

CHART 1

| | 'POULharmu' | 'POULans' |
|---|---|---|
| Petalage. | Semi-double, with 14–16 petals. | Semi-double with 18–26 petals. |
| Color of open bloom. | Red Group 44B. | Red group 53A. |
| Bud form. | Pointed ovoid. | Round with flat top. |

Parents:

*Seed parent.*—Unnamed seedling.

*Pollen parent.*—Unnamed seedling.

Classification:

*Botanical.*—*Rosa hybrida.*

*Commercial.*—Shrub.

FLOWER AND FLOWER BUD

Blooming habit: Continuous.

Flower arrangement: Panicle.

Flower bud:

*Size.*—Upon opening, 20 mm–25 mm in length from base of receptacle to end of bud.

*Bud form.*—Pointed ovoid.

*Bud color.*—As sepals unfold, Red Group 46B. Red Group 53B at ¼ opening.

*Sepals.*—Yellow-Green Group 144A on both upper and lower surfaces of sepal. Moderate to strong foliaceous appendages. Some sepals with strong intonations of Greyed-Purple Group 183A on both upper and lowers surfaces. Surfaces of sepals slightly pubescent on both upper and lower surfaces. Stipitate glands are generally lacking.

*Receptacle.*—Surface: Smooth, with a few white hairs. Shape: Urn-shaped. Size: Medium, 5 mm (h)×5 mm (w). Color: Yellow-Green Group 144A. Strength: Strong.

*Peduncle.*—Surface: Smooth, with a few white hairs. Length: 35 to 40 mm average length. Color: Yellow-Green Group 144A. Strength: Strong.

*Borne.*—Typically, with multiple buds per stem, With 10–15 buds per flowering stem.

Flower bloom:

*Fragrance.*—Little or no fragrance.

*Duration.*—As a cut flower, sprays last 6 to 8 days. The blooms have a duration on the plant of approximately 3 to 5 days. Petals fall cleanly away from plant.

*Size.*—Average flower diameter is 45 mm when open.

*Form.*—Shallow cup.

*Shape of flower when viewed from the side.*—Upon opening, upper part: Convex. Upon opening, lower part: Flattened convex. Open flower, upper part: Flat to flattened convex. Open flower, lower part: Flat to flattened convex.

*Petalage.*—Semi-Double. Average range: 14–16 petals under normal conditions with 1–2 Petaloids.

Color:

*Upon opening, petals.*—Outermost petals: Upper Surface: Red Group 44A and 45B. Reverse Side: Red Group 53C. Upon opening, basal petal spots: Outer Side: Yellow Group 2D. Inner Side: Yellow Group 2C.

*After opening, petals.*—Petals: Upper Surface: Red Group 44B with Red Group 40B overtones. Reverse Side: Red Group 45D. Basal Petal Spots: Outer Side: Yellow Group 1D and White Group 155C. Inner Side: Yellow Group 1D and White Group 155C.

General tonality: On open flower Red Group 44B. No change in the general tonality at the end of the 2nd to 3rd day. Afterwards, general tonality changes gradually to Red Group 44D.

*Petals.*—Petal Reflex: Petals not reflexed, Generally cupped. Petal Edge: Entire. Shape: Deltoid. The petal's apex shape is broadly round. Petal's base shape is pointed. Petaloids: 1–2 Petaloids. Petaloids are very small relative to petals. Petaloids are thin, and colored Red Group 44A. Thickness: Average. Texture: Smooth. Arrangement: Open, not imbricated.

Reproductive organs: Reproductive organs highly visible and decorative on open blooms.

*Pollen.*—Color: Yellow-Orange Group 14B. Quantity: Limited.

*Anthers.*—Size: 3 to 4 mm long. Color: Greyed-Orange Group 169C–169D; when mature, Yellow-Orange Group 14C and Brown Group 200B. Quantity: Moderately abundant.

*Filaments.*—Color: Yellow-Green Group 154D on lower portion, changing to Greyed-Orange Group 163B in top portion.

*Stigmas.*—Size: Stigma is 3 to 4 mm. long. Color: Greyed-Green Group 195C.

*Style.*—Size: Styles are typically 3–5 mm long. Color: Greyed-Green Group 195D.

*Hips.*—None observed.

PLANT

Growth habit: Moderately vigorous, with even, compact growth. When grown as a budded field grown plant on *Rosa multiflora* understock, the average height of the plant itself is 80 cm and the average width is 65 cm.

Stems:

*Color.*—Young wood: Yellow-Green Group 148C. Older wood: Yellow-Green Group 147C.

*Thorns.*—Incidence: Thorns observed in moderate amounts. Size: Two types of thorns, longer thorns deeply concave, shorter thorns finer and linear. Average length: Short, small thorns are 1–2 mm. Longer thorns are 6–7 mm. Color: Mature: Greyed-Orange Group 164B. Immature: Green-Yellow Group 144A, with intonations of Greyed-Orange Group 164B. Shape: Linear to deeply concave.

Plant foliage: Normal numbr of leaflets on leaves in middle of the stem: 5 leaflets.

*Leaf size.*—Small to medium. 65–75 mm (l)×35–45 mm (w).

*Quantity.*—Average.

*Color.*—Upper Leaf Surface: Yellow-Green Group 147A. Lower Leaf Surface: Yellow-Green Group 191A. Juvenile foliage: Yellow-Green Group 146B. Anthocyanin intonation: Location: Mature and immature foliage. Color: Greyed-Red Group 180A.

Plant leaves and leaflets:

*Stipules.*—Size: 12 mm–16 mm. Color: Yellow-Green Group 146B.

*Petiole.*—Length: 22 mm–24 mm. Color: Yellow-Green Group 146B. Underneath: Smooth, with 1 or 2 small prickles. Margins: With stipitate glands.

*Rachis.*—Color: Yellow-Green Group 146B. Underneath: Smooth, With several small prickles. Margins: 3 to 5 stipitate glands observed on margins.

*Leaflet.*—Edge: Serrated. Shape: Ovate. The leaflet's apex is acuminate. The leaflet's base is rounded. Arrangement: The leaflets are arranged in an odd-pinnate formation. Venation: The leaflets are veined in a reticulate pattern. Texture: Upper side of leaflet is moderately glossy. Lower side of leaflet is matte.

Disease resistance: The instant variety is resistant to mildew and black spot under normal growing conditions in Jackson County, Oreg.

Cold hardiness: POULharmu has been found to be cold hardy in USDA Zone 8 and USDA Zone 7.

We claim:

1. A new and distinct variety of rose plant of the shrub class, substantially as herein illustrated and described as a distinct and novel rose variety due to its abundant, orange-red flowers, vigorous growth, disease resistance, and extended period of bloom.

* * * * *

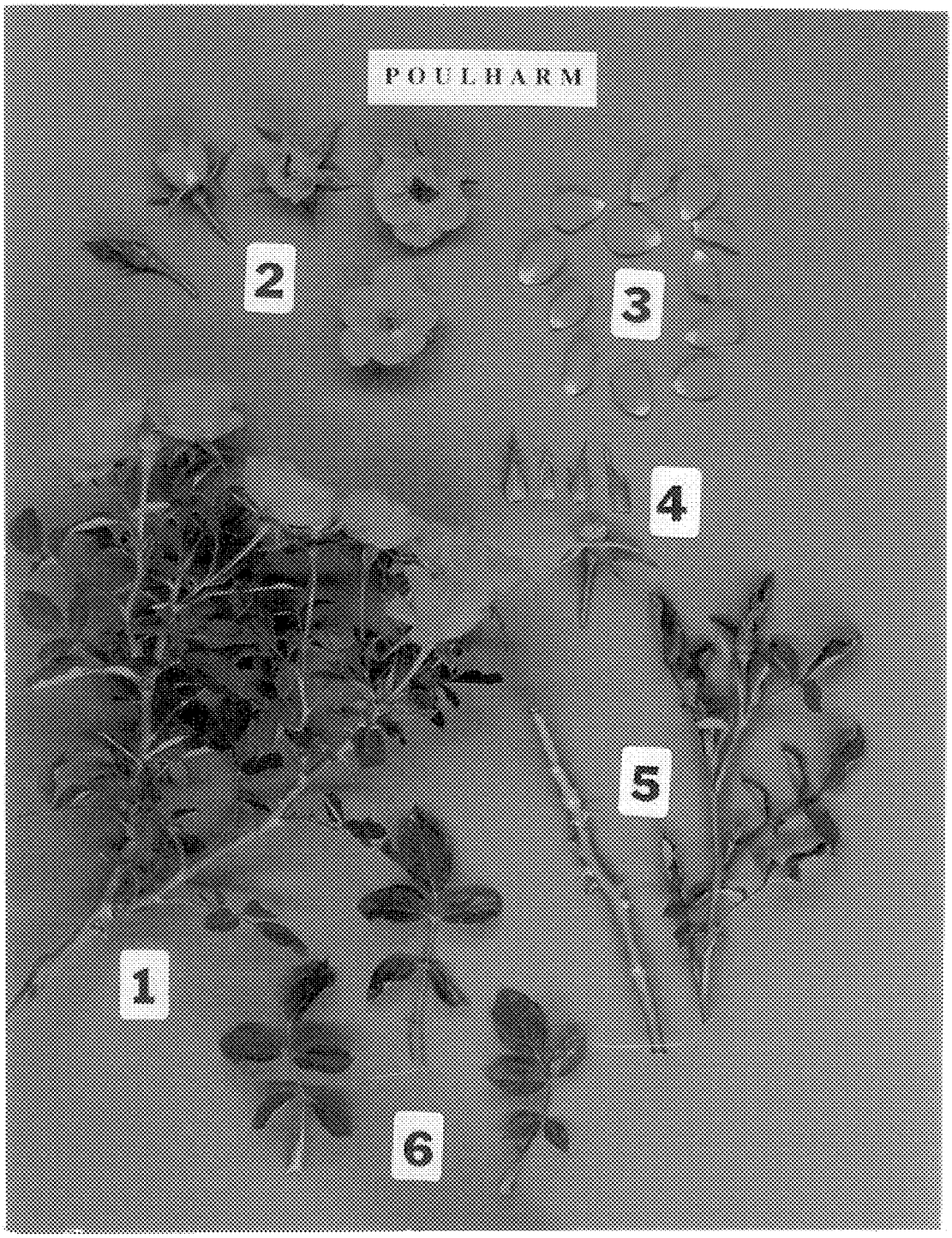
POULHARM
2
3
4
5
1
6